United States Patent [19]
Simpson et al.

[11] Patent Number: 6,133,267
[45] Date of Patent: Oct. 17, 2000

[54] USE OF 2-(2-MORPHOLINOPHENYL) GUANIDINE DERIVATIVES FOR THE TREATMENT OF DIABETES COMPLICATIONS

[75] Inventors: Annemarie Elizabeth Claire Merryman Simpson; Robert Brian Jones, both of Nottingham, United Kingdom

[73] Assignee: Knoll Aktiengesellschaft, Ludwigshafen, Germany

[21] Appl. No.: 09/319,881

[22] PCT Filed: Dec. 8, 1997

[86] PCT No.: PCT/EP97/06831

§ 371 Date: Jun. 14, 1999

§ 102(e) Date: Jun. 14, 1999

[87] PCT Pub. No.: WO98/26782

PCT Pub. Date: Jun. 25, 1998

[30] Foreign Application Priority Data

Dec. 18, 1996 [GB] United Kingdom ............... 9626265

[51] Int. Cl.⁷ .................................................. A61K 31/535
[52] U.S. Cl. .......................................................... 514/239.5
[58] Field of Search ........................................... 514/239.5

[56] References Cited

FOREIGN PATENT DOCUMENTS 2226562  7/1990  United Kingdom .
96/17612  6/1996  WIPO .

OTHER PUBLICATIONS

Richard Bucala, *Diabetes Res. Clin. Prac.*, vol. 30, supp. 1996, pp. S123–S130.

*Primary Examiner*—Raymond Henley, III
*Attorney, Agent, or Firm*—Keil & Weinkauf

[57] ABSTRACT

A compound of formula I

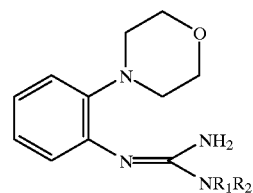

or a pharmaceutically acceptable salt thereof in which $R_1$ and $R_2$ are independently H or methyl (for example 1,1-dimethyl-2-(2-morpholinophenyl)guanidine fumarate) is used for inhibiting the formation of advanced glycosylation end-products, and for the treatment and/or prophylaxis of long-term complications associated with diabetes, such as atherosclerosis, nephropathy, neuropathy and retinopathy.

6 Claims, 2 Drawing Sheets

The effect of 1,1-dimethyl-2-(2-morpholinophenyl)guanidine, aminoguanidine and metformin on advanced glycosylation product formation.

The effect of 1,1-dimethyl-2-(2-morpholinophenyl)guanidine, aminoguanidine and metformin on protein-bound glucose (Amadori) product formation

USE OF 2-(2-MORPHOLINOPHENYL) GUANIDINE DERIVATIVES FOR THE TREATMENT OF DIABETES COMPLICATIONS

This is a 371 of PCT/EP97/06831 filed Dec. 8, 1997.

This invention relates to a method of inhibiting the formation of advanced glycosylation end-products.

According to the present invention there is provided a method of inhibiting the formation of advanced glycosylation end-products comprising administering, to a human in need thereof, a therapeutically effective amount of a compound of formula I

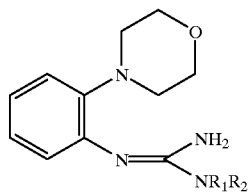

I including pharmaceutically acceptable salts thereof, in which $R_1$ and $R_2$ are independently H or methyl, in conjunction with a pharmaceutically acceptable diluent or carrier.

Compounds of formula I may exist as salts with pharmaceutically acceptable acids. Examples of such salts include hydrochlorides, hydrobromides, sulphates, methanesulphonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid. Compounds of formula I and their salts may exist in the form of solvates (for example hydrates).

Certain compounds of formula I and their salts may exist in more than one crystal form and the present invention includes each crystal form and mixtures thereof. Certain compounds of formula I and their salts may also exist in the form of solvates, for example hydrates, and the present invention includes each solvate and mixtures thereof.

A preferred compound of formula I is 1,1-dimethyl-2(2-morpholinophenyl)guanidine or a salt thereof, preferably the fumarate salt.

The preparation and use of compounds of formula 1, such as 1,1-dimethyl-2(2-morpholinophenyl)guanidine and salts thereof, as hypoglycaemic agents is described in British Patent Specification 2226562. This document discloses data which supports the utility of compounds of formula I in the treatment of hyperglycaemia.

Advanced glycosylation end-products (AGEs) are precursors of protein crosslinking. The formation of AGEs occurs at an accelerated rate in people with elevated blood glucose levels, such as people with impaired glucose tolerance, insulin dependent diabetes mellitus or non-insulin dependent diabetes mellitus. This accelerated rate is due to chronic hyperglycaemia. The accumulation of AGEs contributes to the long-term complications associated with diabetes, such as atherosclerosis, nephropathy, neuropathy and retinopathy. It is therefore desirable to prevent accelerated AGE formation in such people.

Surprisingly, it has now been found that compounds of formula I inhibit the formation of AGEs and therefore have utility in the prophylaxis and treatment of long-term complications associated with diabetes, such as atherosclerosis, nephropathy, neuropathy and retinopathy.

The present invention therefore provides a method of treatment and/or prophylaxis of long-term complications associated with diabetes, such as atherosclerosis, nephropathy, neuropathy and retinopathy, in which a therapeutically effective amount of a compound of formula I

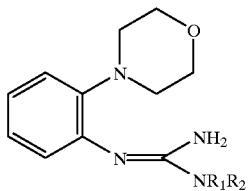

I including pharmaceutically acceptable salts thereof, in which $R_1$ and $R_2$ are independently H or methyl, is administered in conjunction with a pharmaceutically acceptable diluent or carrier to a human in need thereof.

The compound of formula I may be administered in any of the known pharmaceutical dosage forms. The amount of the compound to be administered will depend on a number of factors including the age of the patient, the severity of the condition and the past medical history of the patient and always lies within the sound discretion of the administering physician but it is generally envisaged that the dosage of the compound to be administered will be in the range 10 mg to 3 g, preferably 100 mg to 1 g of free base equivalents per day given in one or more doses.

Oral dosage forms are the preferred compositions for use in the present invention and these are the known pharmaceutical forms for such administration, for example tablets, capsules, granules, syrups and aqueous or oil suspensions. The excipients used in the preparation of these compositions are the excipients known in the pharmacist's art. Tablets may be prepared from a mixture of the active compound with fillers, for example lactose or calcium phosphate; disintegrating agents, for example maize starch or croscarmellose sodium; lubricating agents, for example magnesium stearate; binders, for example microcrystalline cellulose, hydroxypropylmethyl cellulose or polyvinylpyrrolidone and other optional ingredients known in the art to permit tabletting the mixture by known methods. The tablets may, if desired, be coated using known methods and excipients which may include enteric coating using for example hydroxypropylmethylcellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by known methods and, if desired, provided with enteric coatings in a known manner. The contents of the capsule may be formulated using known methods so as to give sustained release of the active compound. The tablets and capsules may conveniently each contain 40 to 500 mg of the active compound.

Other dosage forms for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil. The active compound may be formulated into granules with or without additional excipients. The granules may be ingested directly by the patient or they may be added to a suitable liquid carrier (for example, water) before ingestion. The granules may contain disintegrants, e.g. an effervescent couple formed from an acid and a carbonate or bicarbonate salt to facilitate dispersion in the liquid medium.

The therapeutically active compounds of formula I may be formulated into a composition which the patient retains in his mouth so that the active compound is administered through the mucosa of the mouth.

Dosage forms suitable for rectal administration are the known pharmaceutical forms for such administration, for example, suppositories with cocoa butter or polyethylene glycol bases.

Dosage forms suitable for parenteral administration are the known pharmaceutical forms for such administration, for example sterile suspensions or sterile solutions in a suitable solvent.

Dosage forms for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, e.g. paraffin wax or beeswax, together with a potential transdermal accelerant such as dimethyl sulphoxide or propylene glycol. Alternatively the active compounds may be dispersed in a pharmaceutically acceptable cream, gel or ointment base. The amount of active compound contained in a topical formulation should be such that a therapeutically effective amount of the compound is delivered during the period of time for which the topical formulation is intended to be on the skin.

The therapeutically active compound of formula I may be formulated into a composition which is dispersed as an aerosol into the patients oral or nasal cavity.

Such aerosols may be administered from a pump pack or from a pressurised pack containing a volatile propellant.

The therapeutically active compounds of formula I used in the method of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as an oily suspension of the compound to be infused for example in the form of a free base or other sparingly water-soluble derivative or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The invention further provides the use of compounds of formula I in the manufacture of a medicament for inhibiting the formation of advanced glycosylation end-products. The invention also provides the use of compounds of formula I in the manufacture of a medicament for the treatment and/or prophylaxis of long-term complications associated with diabetes, such as atherosclerosis, nephropathy, neuropathy and retinopathy.

In another aspect, the invention further provides a pharmaceutical composition for inhibiting the formation of advanced giycosylation end-products, comprising a compound of formula I in conjunction with a pharmaceutically acceptable diluent or carrier.

The invention also provides a pharmaceutical composition for the treatment and/or prophylaxis of long-term complications associated with diabetes, such as atherosclerosis, nephropathy, neuropathy and retinopathy comprising a compound of formula I in conjunction with a pharmaceutically acceptable diluent or carrier.

The utility of compounds of formula I in inhibiting the formation of AGEs is illustrated by the following test.

The method is based on that of Brownlee et al, Science 1986; 232: 1629–1632. Solutions were prepared containing Bovine serum albumin (BSA) (100 mg/ml) in sodium phosphate buffer pH 7.4 (500 mM) and incubated with and without $FeCl_2$ (100 $\mu$M). Aminoguanidine HCl (200 mM), metformin (200 mM) or 1,1-dimethyl-2-(2-morpholinophenyl)guanidine (200 mM), together with D-glucose (200 mM), were added to the solutions containing $FeCl_2$.

[$U$-$^{14}C$]-D-glucose (6.12 $\mu$Ci, specific activity 14.6 mCi/mmol; New England Nuclear) was added to each glucose-containing reaction immediately following the removal of reactive contaminants by incubating the radiolabelled glucose in sodium phosphate buffer pH 7.4 (500 mM) containing BSA (100 mg/ml) and $NaBH_3CN$ (20 mM) at 37° C. overnight, then recovering the purified radiolabelled glucose by passing the sample through a Centricon 10 column and a Bio-Rad AG5OX8 column. Sodium azide (3 mM) was added to the reactions, which were then filtered-sterilised using a 0.45 $\mu$m filter. The reactions were incubated in the dark at 37° C. and at the specified times aliquots (100 $\mu$l) were taken for determination of specific advanced glycosylation product fluorescence by the method described in Proc. Natl. Acad. Sci. USA, 1984;81: 583–587, using a Photon Technology International fluorimeter.

Triplicate aliquots (50 $\mu$l) were also taken at each time point for determination of protein-bound glucose. The protein was precipitated overnight with 10% trichloroacetic acid, centrifuged and then washed three times with 5% trichloroacetic acid before being counted in a Tri-carb 2100TR liquid scintillation counter. Protein content was assayed in triplicate using the Coomassie® plus protein assay reagent (Pierce).

In the absence of glucose, BSA (100 mg/ml) has a constant fluorescence of about $3.5 \times 10^5$/mg protein. Following a 0.5 week incubation with glucose the fluorescence of BSA increased in a time-dependent manner, indicating the formation of advanced glycosylation products (AGEs). About a 60% increase in the intensity of luorescence was seen at the 2 week time point. However, in the presence of amino-guanidine HCl (200 mM) a complete inhibition of the advanced glycosylation product formation was evident. 1,1-Dimethyl-2-(2-morpholinophenyl)guanidine (200 mM) caused a marked inhibition on the formation of AGEs, whilst metformin (200 mM) appeared to stimulate AGE formation 1 week following incubation (see FIG. 1).

The protein-bound glucose products, known as Amadori products, as measured by total [$^{14}C$]-glucose incorporation into acid-precipitable protein, also increased in a time-dependent manner when BSA was incubated with glucose (FIG. 2). Aminoguanidine HCl, metformin and 1,1-dimethyl-2-(2-morpholinophenyl)guanidine all inhibited Amadori product formation, with 1,1-dimethyl-2-(2-morpholinophenyl)-guanidine in general showing the greatest inhibition.

Figure 1:
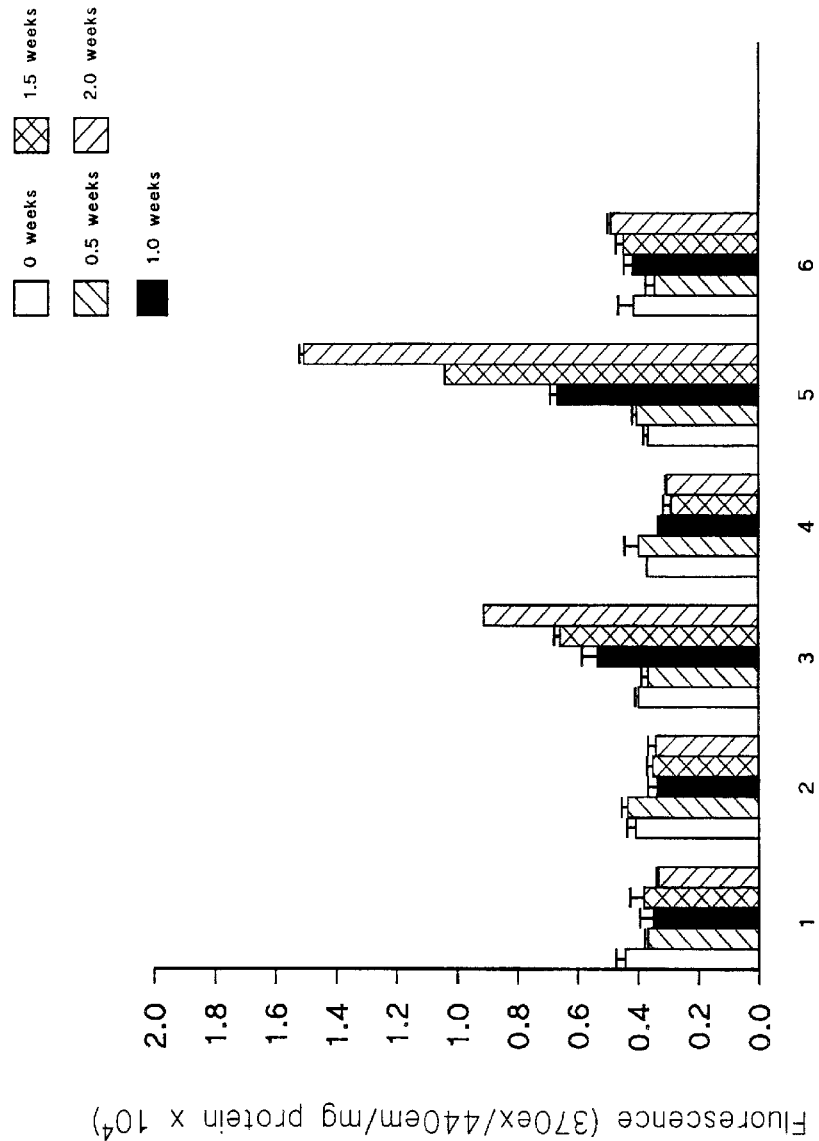
In FIG. 1, (1) represents 100 mg/ml BSA incubated in 500mM sodium phosphate buffer alone, (2) represents buffer plus 100 μM $FeCl_2$, (3) represents buffer plus $FeCl_2$ plus 200 mM D-glucose, (4) represents buffer plus $FeCl_2$ plus 200mM D-glucose plus 200 mM aminoguanidine HCl, (5) represents buffer plus $FeCl_2$ plus 200 mM D-glucose plus 200 mM metformin, and (6) represents buffer plus $FeCl_2$ plus 200 mM D-glucose plus 200 mM 1,1-dimethyl-2-(2-morpholinophenyl)-guanidine. At selected time intervals aliquots were removed and the advanced glycosylation product fluorescence and protein content were determined. The results are expressed as means (n=3)±SD.
Figure 2:
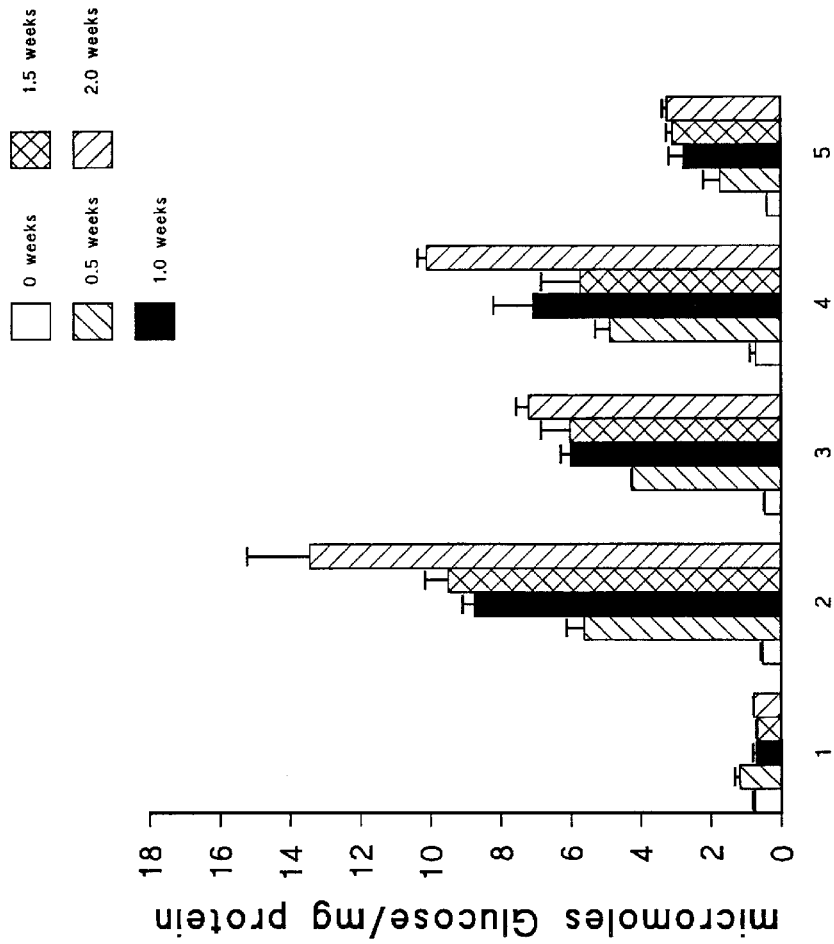
In FIG. 2, (1) represents 200 mM D-glucose incubated alone in 500 mM sodium phosphate buffer, (2) represents 100 mg/ml BSA incubated in either buffer, 100 μM $FeCl_2$ plus 200 mM D-glucose, (3) represents buffer plus $FeCl_2$ plus 200 mM D-glucose plus 200 mM aminoguanidine HCl, (4) represents buffer plus $FeCl_2$ plus 200 mM D-glucose plus 200 mM metformin, and (5) represents buffer plus $FeCl_2$ plus 200 mM D-glucose plus 200 mM 1,1-dimethyl-2-(2-morpholinophenyl)guanidine. All reactions contained 6.12 μCi [$^{14}$C-]D-glucose. At selected time intervals aliquots were removed and the protein-bound glucose and protein content were determined. The results are expressed as means (n=3)±SD.

These data provide evidence of the utility of compounds of formula I in inhibiting the formation of advanced glycosylation end-products, and support for their use in the treatment and/or prophylaxis of long-term complications associated with diabetes, such as atherosclerosis, nephropathy, neuropathy and retinopathy.

What is claimed is:

1. A method of inhibiting the formation of advanced glycosylation end-products comprising administering to a human in need thereof a therapeutically effective amount of a compound of formula I

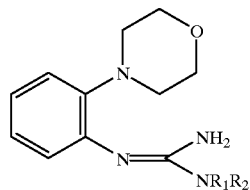

including pharmaceutically acceptable salts thereof in which $R_1$ and $R_2$ are independently H or methyl, in conjunction with a pharmaceutically acceptable diluent or carrier.

2. A method of treatment and/or prophylaxis of long-term complications associated with diabetes, such as atherosclerosis, nephropathy, neuropathy and retinopathy, comprising administering to a human in need thereof a therapeutically effective amount of a compound of formula I

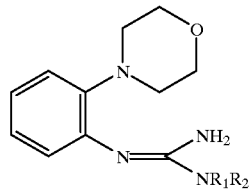

including pharmaceutically acceptable salts thereof in which $R_1$ and $R_2$ are independently H or methyl, in conjunction with a pharmaceutically acceptable diluent or carrier.

3. A method of claim 1 wherein the compound of formula I is 1,1-dimethyl-2-(2-morpholinophenyl)guanidine or a pharmaceutically acceptable salt thereof.

4. A method of claim 1 wherein the compound of formula I is 1,1-dimethyl-2-(2-morpholinophenyl)guanidine fumarate.

5. The method of claim 2 wherein the compound of formula I is 1, 1-dimethyl-2-(2-morpholinophenyl) guanidine or a pharmacetutically acceptable salt thereof.

6. The method of claim 3 wherein the compound of formula I is 1,1-dimethyl-2-(2-morpholinophenyl)guanidine furmarate.

* * * * *

UNITED STATES PATENT AND TRADEMARK OFFICE
CERTIFICATE OF CORRECTION

PATENT NO.: 6,133,267

DATED: October 17, 2000

INVENTOR(S): SIMPSON et al.

It is certified that error appears in the above-identified patent and that said Letters Patent is hereby corrected as shown below:

Col. 6, claim 3, line 35, "A" should be --The--.

Col. 6, claim 4, line 38, "A" should be --The--.

Signed and Sealed this

Eighth Day of May, 2001

*Attest:*

NICHOLAS P. GODICI

*Attesting Officer*      *Acting Director of the United States Patent and Trademark Office*